(12) United States Patent
Hasegawa et al.

(10) Patent No.: US 8,940,872 B2
(45) Date of Patent: Jan. 27, 2015

(54) ANTIBODY BINDING SPECIFICALLY TO TDP-43 AGGREGATE

(75) Inventors: Masato Hasegawa, Chofu (JP); Tetsuaki Arai, Tokyo (JP); Takashi Nonaka, Tokyo (JP); Fuyuki Kametani, Atsugi (JP); Haruhiko Akiyama, Hachioji (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 894 days.

(21) Appl. No.: 12/667,624

(22) PCT Filed: Jul. 7, 2008

(86) PCT No.: PCT/JP2008/062650
§ 371 (c)(1),
(2), (4) Date: Jan. 4, 2010

(87) PCT Pub. No.: WO2009/008529
PCT Pub. Date: Jan. 15, 2009

(65) Prior Publication Data
US 2011/0287453 A1    Nov. 24, 2011

(30) Foreign Application Priority Data
Jul. 6, 2007  (JP) ................................ 2007-178583

(51) Int. Cl.
C07K 16/00   (2006.01)
C07K 16/18   (2006.01)
G01N 33/68   (2006.01)

(52) U.S. Cl.
CPC ............ *C07K 16/18* (2013.01); *G01N 33/6875* (2013.01)
USPC ................. 530/387.9; 530/388.85; 530/389.1

(58) Field of Classification Search
CPC .... C07K 14/4711; C07K 14/47; C07K 16/18; C07K 14/435; C07K 2317/56; G01N 2800/2821; G01N 33/6896
See application file for complete search history.

(56) References Cited

U.S. PATENT DOCUMENTS 5,688,511 A  * 11/1997 Gaynor et al. ............. 424/207.1
2002/0086009 A1    7/2002 Ishiguro et al.
2009/0263824 A1*  10/2009 Lee et al. ........................ 435/7.1
2010/0136573 A1*   6/2010 Petrucelli et al. .............. 435/7.1

FOREIGN PATENT DOCUMENTS

WO    WO-97/34145 A1    9/1997
WO    WO 2009/044119 A1  4/2009

OTHER PUBLICATIONS

Mckenzie et al. Pathological TDP-43 distinguishes sporadic amyotrophic lateral sclerosis from amyotrophic lateral sclerosis with SOD1 mutations. Ann Neuron 2007, vol. 61, pp. 427-434.*
Omi et al., "Shinpan Ko Peptide Kotai Jikken Protocol—Idenshi Sanbutsu no Dotei kara Tanpakushitsu Kino Kalseki Made", 2$^{nd}$ Edition, Shujunsha Co., Ltd., Sep. 6, 2004, pp. 106-129.
Neumann et al., "Ubiquitinated TDP-43 in Frontotemporal Lobar Degeneration and Amyotrophic Lateral Sclerosis", Science, Oct. 6, 2006, pp. 130-133, vol. 314, No. 5796.
Arai et al., "TDP-43 is a Component of Ubiquitin-Positive Tau-Negative Inclusions in Frontotemporal Lobar Degeneration and Amyotrophic Lateral Sclerosis", ScienceDirect, Biochemical and Biophysical Research Communications, Dec. 22, 2006, pp. 602-611, vol. 351, No. 3, Elsevier.
Hasegawa et al., "TDP-43 is Deposited in the Guam Parkinsonism-Dementia Complex Brains", Brain, May 2007, pp. 1386-1394, vol. 130, Pt. 5, Oxford University Press.
Fujiwara et al., "α- Synuciein is Phosphorylated in Synucleinopathy Lesions", Nature Cell Biology, Feb. 2002, pp. 160-164, vol. 4.
Morishima-Kawashima et al., "Proline-Directed and Non-Proline-Directed Phosphorylation of PHF-tau", The Journal of Biological Chemistry, Jan. 13, 1995, pp. 823-829, vol. 270, No. 2.
Extended European Search Report dated Aug. 26, 2010, issued in European Patent Application No. 08778121.7.
Forman et al., "TDP-43: a novel neurodegenerative proteinopathy," Current Opinion in Neurobiology, vol. 17, pp. 548-555, 2007.
Hasegawa et al., "Phosphorylated TDP-43 in Frontotemporal Lobar Degeneration and Amyotrophic Lateral Sclerosis," Ann. Neurol., vol. 64, pp. 60-70, 2008.
Nagata et al., "A decade of site- and phosphorylation state-specific antibodies: recent advances in studies of spatiotemporal protein phosphorylation," Genes to Cells, vol. 6, pp. 653-664, 2001.
U.S. Appl. No. 60/932,656, filed Jun. 1, 2007.

* cited by examiner

*Primary Examiner* — Shafiqul Haq
(74) *Attorney, Agent, or Firm* — Birch, Stewart, Kolasch & Birch, LLP

(57) ABSTRACT

The present invention provides an antibody that specifically binds to an abnormal TDP-43 protein aggregate, an agent comprising the antibody for detecting a TDP-43 proteinopathy lesion, and a method for detecting or diagnosing a TDP-43 proteinopathy lesion by using the antibody.

11 Claims, 8 Drawing Sheets

SEQUENCE LISTING

```
<160> NUMBER OF SEQ ID NOS: 13

<210> SEQ ID NO 1
<211> LENGTH: 414
<212> TYPE: PRT
<213> ORGANISM: Homo sapiens

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60
```

```
Asp Ala Gly Trp Gly Asn Leu Val Tyr Val Asn Tyr Pro Lys Asp
 65                  70                  75                  80

Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 2
<211> LENGTH: 10
<212> TYPE: PRT
<213> ORGANISM: Artificial
<220> FEATURE:
<223> OTHER INFORMATION: synthetic peptide

<400> SEQUENCE: 2

Ala Ser Asn Ala Gly Ser Gly Ser Gly Phe
1               5                   10
```

```
<210> SEQ ID NO 3
<211> LENGTH: 11
<212> TYPE: PRT
<213> ORGANISM: Artificial
<220> FEATURE:
<223> OTHER INFORMATION: synthetic peptide

<400> SEQUENCE: 3

Asn Gly Gly Phe Gly Ser Ser Met Asp Ser Lys
1               5                   10

<210> SEQ ID NO 4
<211> LENGTH: 10
<212> TYPE: PRT
<213> ORGANISM: Artificial
<220> FEATURE:
<223> OTHER INFORMATION: synthetic peptide

<400> SEQUENCE: 4

Met Asp Ser Lys Ser Ser Gly Trp Gly Met
1               5                   10

<210> SEQ ID NO 5
<211> LENGTH: 11
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 5

Cys Ala Ser Asn Ala Gly Ser Gly Ser Gly Phe
1               5                   10

<210> SEQ ID NO 6
<211> LENGTH: 12
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 6

Cys Asn Gly Gly Phe Gly Ser Ser Met Asp Ser Lys
1               5                   10

<210> SEQ ID NO 7
<211> LENGTH: 12
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (8)..(8)
<223> OTHER INFORMATION: PHOSPHORYLATION

<400> SEQUENCE: 7

Cys Asn Gly Gly Phe Gly Ser Ser Met Asp Ser Lys
1               5                   10
```

```
<210> SEQ ID NO 8
<211> LENGTH: 12
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (7)..(8)
<223> OTHER INFORMATION: PHOSPHORYLATION

<400> SEQUENCE: 8

Cys Asn Gly Gly Phe Gly Ser Ser Met Asp Ser Lys
1               5                   10

<210> SEQ ID NO 9
<211> LENGTH: 11
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (6)..(6)
<223> OTHER INFORMATION: PHOSPHORYLATION

<400> SEQUENCE: 9

Cys Met Asp Ser Lys Ser Ser Gly Trp Gly Met
1               5                   10

<210> SEQ ID NO 10
<211> LENGTH: 11
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 10

Cys Met Asp Ser Lys Ser Ser Gly Trp Gly Met
1               5                   10

<210> SEQ ID NO 11
<211> LENGTH: 11
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (6)..(7)
<223> OTHER INFORMATION: PHOSPHORYLATION

<400> SEQUENCE: 11

Cys Met Asp Ser Lys Ser Ser Gly Trp Gly Met
1               5                   10

<210> SEQ ID NO 12
<211> LENGTH: 4
<212> TYPE: PRT
<213> ORGANISM: Artificial
<220> FEATURE:
<223> OTHER INFORMATION: phosphorylated consensus sequence
<220> FEATURE:
<221> NAME/KEY: MOD_RES
<222> LOCATION: (1)..(1)
<223> OTHER INFORMATION: PHOSPHORYLATION
<220> FEATURE:
```

```
<221> NAME/KEY: MISC_FEATURE
<222> LOCATION: (1)..(1)
<223> OTHER INFORMATION: Xaa stands for Ser or Thr
<220> FEATURE:
<221> NAME/KEY: MISC_FEATURE
<222> LOCATION: (2)..(3)
<223> OTHER INFORMATION: Xaa stands for any amino acid residue
<220> FEATURE:
<221> NAME/KEY: MISC_FEATURE
<222> LOCATION: (4)..(4)
<223> OTHER INFORMATION: Xaa stands for Ser or Thr

<400> SEQUENCE: 12

Xaa Xaa Xaa Xaa
1

<210> SEQ ID NO 13
<211> LENGTH: 5
<212> TYPE: PRT
<213> ORGANISM: Artificial
<220> FEATURE:
<223> OTHER INFORMATION: phosphorylated consensus sequence
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MISC_FEATURE
<222> LOCATION: (1)..(1)
<223> OTHER INFORMATION: Xaa stands for Ser or Thr
<220> FEATURE:
<221> NAME/KEY: MISC_FEATURE
<222> LOCATION: (2)..(4)
<223> OTHER INFORMATION: Xaa stands for any amino acid residue
<220> FEATURE:
<221> NAME/KEY: MISC_FEATURE
<222> LOCATION: (5)..(5)
<223> OTHER INFORMATION: Xaa stands for Ser or Thr

<400> SEQUENCE: 13

Xaa Xaa Xaa Xaa Xaa
1               5
```

ANTIBODY BINDING SPECIFICALLY TO TDP-43 AGGREGATE

TECHNICAL FIELD

The present invention relates to an antibody that binds specifically to an abnormal TDP-43 protein aggregate, to an agent and a method comprising the antibody for detecting a TDP-43 proteinopathy lesion, and to a pharmaceutical composition for treating a TDP-43 proteinopathy.

BACKGROUND ART

TDP-43 (TAR DNA-binding protein of 43 kDa) is known as a nuclear factor that binds to TAR (transactivation responsive region) DNA and that is involved in transcriptional modulation and alternative splicing.

In addition, TDP-43 is a protein that aggregates and accumulates in degenerated nerve cells such as those of frontotemporal lobar degeneration (FTLD) including frontotemporal dementia, in a form of a ubiquitin-positive intracellular inclusion (NCI), a degenerated spicular structure or the like (Arai T et al., Biochem Biophys Res Commun. 2006 Dec. 22; 351(3):602-11. Epub 2006 Oct. 30, Neumann M et al., Science. 2006 Oct. 6; 314(5796):130-3). Other than FTLD, TDP-43 is also known to accumulated in the nerve cells and glial cells of amyotrophic lateral sclerosis (ALS), Parkinson-dementia complex in Guam, Parkinson-dementia complex in Kii peninsula and the like. These diseases are collectively named as TDP-43 proteinopathies (TDP-43 protein storage diseases). Abnormal accumulation of TDP-43 is observed at the site of lesions of each disease which appears to imply close involvement in the cause of nerve degeneration in these diseases.

Presently, two types of commercially available antibodies are used for the studies on TDP-43 and the pathological diagnosis of TDP-43 proteinopathies. These antibodies, however, are known to bind not only to abnormally accumulated TDP-43 in the brain or spinal cord of a patient but also strongly to normal TDP-43 in the brain, spinal cord or the like, thereby rendering normal TDP-43 in the nuclear to be stained upon immunostaining of the brain or spinal cord specimens.

Meanwhile, although highly phosphorylated TDP-43 was found to accumulate in the brain or spinal cord of a patient (Arai T et al., Biochem Biophys Res Commun. 2006 Dec. 22; 351(3):602-11. Epub 2006 Oct. 30, Neumann M et al., Science. 2006 Oct. 6; 314(5796):130-3), there is no report as to the site of the phosphorylation or the enzyme involved in the phosphorylation.

DISCLOSURE OF INVENTION

The present invention was accomplished in view of such circumstances, and the problems to be solved by the invention are to provide an antibody that binds specifically to an abnormal TDP-43 protein aggregate, an agent and a method comprising the antibody for detecting a TDP-43 proteinopathy lesion, and a pharmaceutical composition for treating a TDP-43 proteinopathy.

As a result of keen examination for solving the above problems, we found that TDP-43 (a component of ubiquitin-positive inclusions) abnormally accumulated in degenerated nerve cells, has a part of its constituent amino acids phosphorylated. We also found that an antibody prepared by using a synthetic peptide comprising this phosphorylated amino acid as an antigen can specifically bind to an abnormal TDP-43 protein aggregate, thereby accomplishing the present invention.

Thus, the present invention is as follows.

(1) An antibody that binds specifically to the following protein (a) or (b) or peptide (c):

(a) a protein comprising an amino acid sequence in which at least one amino acid residue of the amino acid sequence represented by SEQ ID NO:1 is phosphorylated;

(b) a protein comprising a mutated amino acid sequence in which one or more amino acid residues are deleted, substituted, inserted or added in the amino acid sequence represented by SEQ ID NO:1, and having TDP-43 activity, wherein at least one amino acid residue of the mutated amino acid sequence is phosphorylated; or (c) a partial peptide comprising a partial amino acid sequence containing the phosphorylated amino acid residue of the amino acid sequence of the protein (a) or (b) above.

(2) The antibody according to (1), wherein said at least one amino acid residue is at least one selected from the group consisting of a serine residue, a threonine residue and a tyrosine residue.

(3) The antibody according to either one of (1) and (2), wherein said at least one amino acid residue is at least one selected from the group consisting of amino acid residues 393, 403, 404, 409 and 410 of the amino acid sequence represented by SEQ ID NO:1.

(4) The antibody according to any one of (1) to (3), wherein the amino acid sequence of the peptide is represented by any one of SEQ ID NOS:5-11.

(5) The antibody according to any one of (1) to (4), which can bind to a site of the protein (a) or (b) or the partial peptide (c) that has been structurally altered by phosphorylation.

(6) The antibody according to any one of (1) to (5), wherein the phosphorylation is induced by casein kinase 1.

(7) The antibody according to any one of (1) to (6) wherein the antibody is a monoclonal antibody.

(8) The antibody according to any one of (1) to (6) wherein the antibody is a polyclonal antibody.

(9) A monoclonal antibody produced with a hybridoma assigned Accession Number FERM ABP-10984. The hybridoma was deposited with the International Patent organism Depository Center of the National Institute of Advanced industrial Science and Technology (Central 6, 1-1-1, Higashi, Tsukuba, Ibaraki) on Jul. 3, 2008.

(10) An antibody that binds to an antigen determinant to which the antibody according to any one of (7) to (9) binds.

(11) The antibody according to any one of (7), (9) and (10) wherein the antibody is a chimeric antibody, a human type antibody or a humanized antibody.

(12) A hybridoma that produces the antibody according to any one of (7), and (9) to (11).

(13) A hybridoma assigned Accession Number FERM ABP-10984.

(14) An agent for detecting phosphorylated TDP-43, comprising the antibody according to any one of (1) to (11).

(15) An agent for detecting a TDP-43 proteinopathy lesion, comprising the antibody according to any one of (1) to (11).

(16) An agent for diagnosing a TDP-43 proteinopathy, comprising the antibody according to any one of (1) to (11).

(17) A pharmaceutical composition comprising the antibody according to any one of (1) to (11) as an active element.

(18) A method for detecting a TDP-43 proteinopathy lesion, comprising allowing reaction between the antibody according to any one of (1) to (11) and a collected test sample.

(19) Use of the antibody according to any one of (1) to (11), for producing the detecting agent according to (14) or (15), the diagnosis agent according to (16), or the pharmaceutical composition according to (17).

The present invention provides an antibody that binds specifically to an abnormal TDP-43 protein aggregate, an agent and a method comprising the antibody for detecting a TDP-43 proteinopathy lesion, a pharmaceutical composition for treating a TDP-43 proteinopathy, and the like.

Since the antibody of the present invention can specifically bind to an abnormal TDP-43 protein aggregate found in patients with a TDP-43 proteinopathy such as FTLD or ALS, the antibody is useful for diagnosis and treatment of these diseases.

BEST MODE FOR CARRYING OUT THE INVENTION

Figure 1:
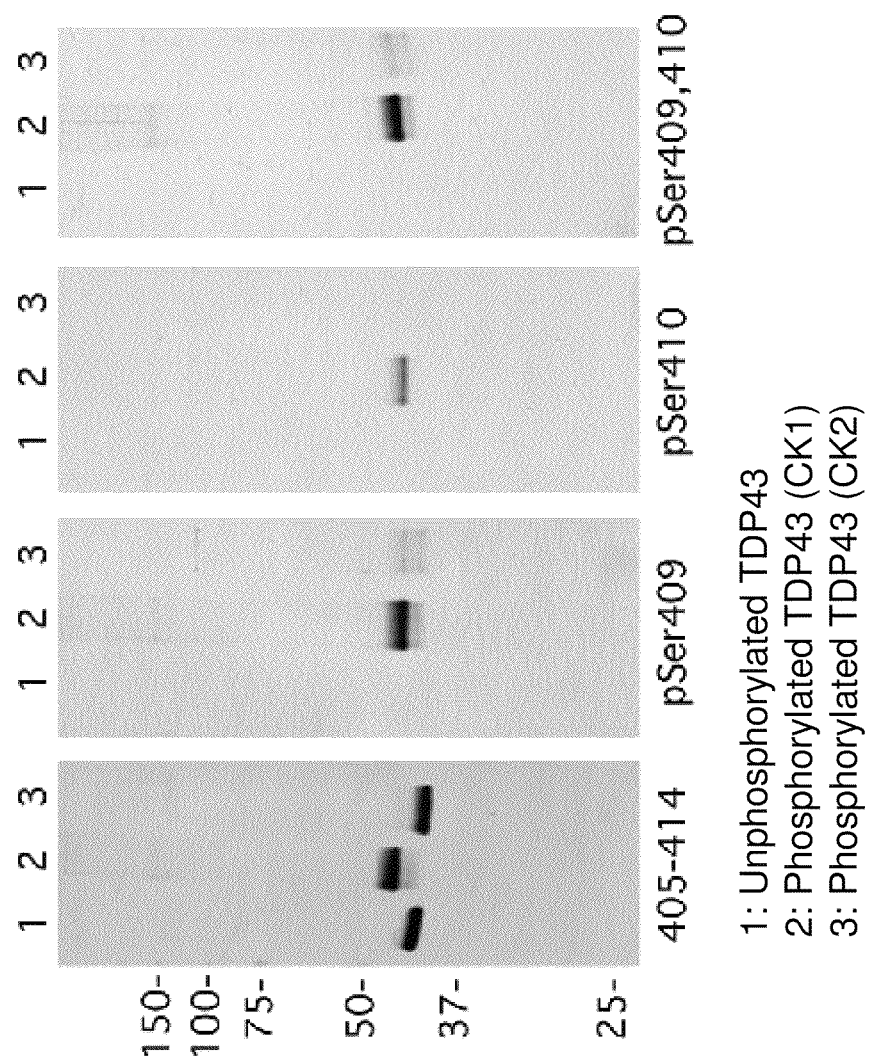
FIG. 1 is a view showing the results from an analysis of the specificity of an antibody of the present invention by western blotting.

Hereinafter, the present invention will be described in details. The following embodiment is an example for illustrating the present invention, which is not intended to limit the present invention. The present invention may be carried out in various embodiments without departing from the scope of the invention.

All of the literatures, laid-open patent publications, patent publications and other patent documents cited herein are incorporated herein by reference. The present specification incorporates the entire content of the specification and drawings of Japanese Patent Application Publication (Tokugan) No. 2007-178583 filed on Jul. 6, 2007 based on which the present application claims priority.

1. Summary

The present invention relates to an antibody that binds specifically to phosphorylated TDP-43, an agent and a method comprising the antibody for detecting a TDP-43 proteinopathy lesion, a pharmaceutical composition for treating a TDP-43 proteinopathy, and the like.

TDP-43 abnormally accumulates in nerve cells of the brain or spinal cord of a TDP-43 proteinopathy patient, and forms abnormal TDP-43 protein aggregates such as ubiquitin-positive intracellular inclusions (NCI) and degenerated spicular structures. The abnormal TDP-43 protein aggregates are also highly phosphorylated. The aggregated and accumulated TDP-43 takes a form of a filamentous structure, which implies that the original structure of TDP-43 has been altered to a beta-sheet-rich conformation upon phosphorylation.

The present inventors focused on the fact that a part of the constituent amino acids of abnormally accumulated TDP-43 is phosphorylated, and found that an antibody prepared by using a synthetic peptide having the phosphorylated amino acids as an antigen specifically binds to an abnormal TDP-43 protein aggregate, thereby accomplishing the present invention. According to the present invention, an antibody of the invention was also found to bind to a part of TDP-43 structure altered by phosphorylation.

The present inventors further found that TDP-43 can be a substrate of casein kinase 1 (CK1), and that most of the substrate-binding sites were also phosphorylated in the patient's brain. Accordingly, a site of the amino acid sequence of TDP-43 which matches a phosphorylated consensus sequence of CK1 (pS/T-X-X-S/T, pS/T-X-X-X-S), namely, a site of the amino acid sequence of TDP-43, where CK1 binds and which undergoes phosphorylation is presumably a site where the antibody of the present invention binds well.

While an antibody of the present invention does not bind to unphosphorylated TDP-43, it can specifically bind to phosphorylated TDP-43 and peptides having a part thereof. Hence, the antibody of the present invention is useful in diagnosing and treating a TDP-43 proteinopathy such as FTLD and ALS.

2. Antibody that Binds Specifically to Phosphorylated TDP-43

An "antibody" of the present invention refers to the above-mentioned antibody that specifically binds to phosphorylated TDP-43 or a fragment thereof, which may be either a polyclonal antibody or a monoclonal antibody. Herein, an antibody or a fragment thereof that specifically bind to phosphorylated TDP-43 or a partial peptide of phosphorylated TDP-43 is referred to as an "anti-phosphorylated-TDP-43 antibody".

An antibody of the present invention also comprises an antibody that binds to an antigen determinant (epitope) which binds with the antibody of the present invention. The antigen determinant is an entire or partial region of phosphorylated TDP-43 including the above-mentioned site matching, for example, the phosphorylated consensus sequences of CK1 (pS/T-X-X-SIT, pS/T-X-X-X-S), i.e., a site of TDP-43 amino acid sequence, which binds with CK1 and undergoes phosphorylation.

According to the present invention, the phrase "specifically binds" means that binding (reaction) takes place with a phosphorylated TDP-43 protein or a TDP-43 peptide (containing a site structurally altered by phosphorylation), but not with an unphosphorylated protein or peptide. Whether or not the binding is specific may be confirmed by an immunological technique such as ELISA assay, western blot assay or immunohistological staining.

The antibody of the present invention comprises an antibody fragment. Examples of antibody fragments include peptides containing at least Fab (antigen-binding fragment), F(ab')$_2$, Fab', Fv, diabody (dibodies), dsFv, linear antibody, scFv (single chain Fv), or complementarity determining region (CDR) as a part thereof. Even if an amino acid sequence of the antibody is modified, such an antibody lies within the scope of the present invention as long as it can specifically bind to the above-described phosphorylated TDP-43 or phosphorylated TDP-43 partial peptide.

An antibody of the present invention also comprises a chimeric antibody, a human type antibody and a humanized antibody.

3. Production of Antibody

Hereinafter, a method for preparing an anti-phosphorylated-TDP-43 antibody will be described.

(1) Preparation of Antigen (1-1) Full-length TDP-43

Phosphorylated TDP-43 is used as an immunogen for preparing an antibody of the present invention. A peptide containing a partial amino acid sequence of the full-length sequence of the above-described phosphorylated TDP-43 can also be used as an antigen.

Here, examples of the phosphorylated TDP-43 include the following proteins (a) and (b).

(a) a protein comprising an amino acid sequence having at least one amino acid residue phosphorylated in the amino acid sequence represented by SEQ ID NO:1.

(b) a protein comprising a mutated amino acid sequence having one or more amino acid residues deleted, substituted, inserted or added in the amino acid sequence represented by SEQ ID NO:1, and having TDP-43 activity, wherein at least one amino acid residue of the mutated amino acid sequence is phosphorylated.

Specifically, according to the present invention, other than the amino acid sequence region of phosphorylated TDP-43 used as an antigen represented by SEQ ID NO:1, phosphorylated TDP-43 having the following mutated amino acid sequences (i) to (iv) may also be used.

(i) an amino acid sequence having one or several (for example, 1 to 10, more preferably 1 to 5) amino acids deleted from the amino acid sequence represented by SEQ ID NO:1;

(ii) an amino acid sequence having one or several (for example, 1 to 10, more preferably 1 to 5) amino acids of the amino acid sequence represented by SEQ ID NO:1 substituted with other amino acids;

(iii) an amino acid sequence having one or several (for example, 1 to 10, more preferably 1 to 5) other amino acids added to or inserted into the amino acid sequence represented by SEQ ID NO:1.

According to the present invention, a mutant TDP-43 having an amino acid sequence including a combination of (i) to (iii) above, and having similar action as the above-described TDP-43 activity may also be used.

Here, the term "TDP-43 activity" refers to an activity of binding to a nucleic acid having TG (thymine-guanine) or UG (uracil-guanine) repeat. Such a binding activity may be measured by performing UV crosslinking and a competitive inhibition test thereof, or by known EMSA assay.

TDP-43 used with the present invention may also be a protein having homology with the above-described amino acid sequence as long as it has TDP-43 activity. Examples of such proteins include amino acid sequences having 85% or more, preferably 90% or more, more preferably 95% or more homology with the amino acid sequence represented by SEQ ID NO:1.

DNA coding for such an amino acid sequence having one or several amino acids deleted, substituted, inserted or added in the amino acid sequence represented by SEQ ID NO:1 may be prepared by using a nucleotide sequence of DNA coding for TDP-43 according to a method such as site-directed mutagenesis described in "Molecular Cloning, A Laboratory Manual 2nd ed." (Cold Spring Harbor Laboratory Press (1989)), Kunkel (1985) Proc. Natl. Acad. Sci. USA 82: 488-92, Kunkel (1988) Method. Enzymol. 85: 2763-6.

Mutation may be introduced into DNA by using a mutagenesis kit utilizing site-directed mutagenesis such as Kunkel method or Gapped duplex method, for example, QuikChange™ Site-Directed Mutagenesis Kit (Stratagene), GeneTailor™ Site-Directed Mutagenesis System (Invitrogen), TaKaRa Site-Directed Mutagenesis System (Mutan-K, Mutan-Super Express Km, etc.: Takara Bio) or the like.

Thereafter, the TDP-43 protein of interest may be obtained with a host-expression system by using a general genetic engineering procedure (Molecular Cloning, A Laboratory Manual 2nd ed. (Cold Spring Harbor Laboratory Press (1989)).

An amino acid residue targeted for phosphorylation is not particularly limited, but preferably at least one selected from the group consisting of a serine (Ser) residue, a threonine (Thr) residue and a tyrosine (Tyr) residue.

Examples of sites containing the above-described phosphorylated consensus sequence (pSer/Thr-X-X-Ser/Thr (SEQ ID NO:12) or pSer/Thr-X-X-X-Ser (SEQ ID NO:13)) (X represents any amino acid, while pSer/Thr represents serine or threonine that is phosphorylated in the sequence) include the following amino acids among the amino acid sequence represented by SEQ ID NO:1:

Thr25 (representing the 25th Thr; Similar rule shall apply hereinafter), Ser29, Thr141, Thr153, Ser180, Ser254, Ser347, Ser369, Ser373, Ser375, Ser389, Ser403, Ser404 and Ser407.

According to the present invention, one or more amino acid residues among 393rd, 403rd, 404th, 409th and 410th amino acids (Ser or Thr) of the amino acid sequence represented by SEQ ID NO:1, are preferably phosphorylated. In the case of the above-mentioned mutated amino acid sequence, those having one or more amino acid residues phosphorylated at positions corresponding to the amino acid sequence represented by SEQ ID NO:1, namely, the 393rd, 403rd, 404th, 409th and 410th amino acid residues (Ser or Thr) may be used as an antigen.

Herein, in order to indicate the amino acid sequence represented by SEQ ID NO:1 and the positions thereof, an amino acid may be indicated by three- or one-letter code following the number of its position. For example, when the 393rd amino acid of the amino acid sequence represented by SEQ ID NO:1 is serine, it is indicated as "Ser393" or "S393". Similarly, when the 403rd amino acid residue is serine, it may be represented as "Ser403" or "S403". Other amino acid residues and their positions are also indicated according to this notation.

A method for phosphorylating an amino acid residue may be performed by mixing a substrate solution containing TDP-43 with casein kinase 1 (CK1), casein kinase 2 (CK2), other phosphoenzyme or a crude enzyme solution containing them and ATP, and incubating the resultant for a few minutes to several tens of hours, thereby phosphorylating TDP-43. The substrate solution containing TDP-43 may be obtained by a method in which a cell obtained by introducing a plasmid containing TDP-43 into *E. coli* or a cultured cell is proliferated. Apart from this method, the solution may be synthesized in a test tube or prepared from a biomaterial. Not only full-length TDP-43, but also a partial degradation product or a partial peptide may alternatively be used as a substrate for phosphorylation using the above-mentioned enzyme.

(1-2) Partial Peptide of Phosphorylated TDP-43

According to the present invention, other than full-length phosphorylated TDP-43, a partial fragment having a part of the length may be used as an antigen as long as it contains a phosphorylated site (a phosphorylated amino acid residue). According to the present invention, such a partial fragment having a part of the length is referred to as "a partial peptide". Peptides comprise polypeptides. According to the present invention, they are collectively referred to as "partial peptides" regardless of the lengths of their amino acid sequences as long as they have a part of the sequence of phosphorylated TDP-43 and having at least one amino acid residue phosphorylated.

According to the present invention, an amino acid sequence of a partial peptide preferable for use as an antigen is a part of the amino acid sequence of the protein (a) or (b) described in item (1-1) above containing the phosphorylated amino acid residue, which preferably contains successive four or more amino acids. More preferably, a partial peptide is a sequence consisting of 8-15 amino acids of the amino acid sequence represented by SEQ ID NO:1, and more preferably a sequence consisting of 10-11 amino acids of the amino acid sequence represented by SEQ ID NO:1. According to the results from neuropathological and biochemical analyses, a partial peptide preferably has a partial sequence of the C-terminal of the amino acid sequence represented by SEQ ID NO:1. Examples of such partial sequences include the following peptides represented by SEQ ID NOS:2-4.

```
Peptides 388-397: ASNAGSGSGF     (SEQ ID NO: 2)

Peptides 398-408: NGGFGSSMDSK    (SEQ ID NO: 3)

Peptides 405-414: MDSKSSGWGM     (SEQ ID NO: 4)
```

The amino acid sequences represented by SEQ ID NOS:2, 3 and 4 are the amino acids 388-397, 398-408 and 405-414 of the amino acid sequence represented by SEQ ID NO:1, respectively. A partially modified version of the above-described partial sequence may also be used in the present invention. For example, in order to crosslink a carrier protein such as Keyhole Limpet Hemocyanin (KLH) or thyroglobulin, a cysteine (Cys) residue may be linked to the N- or C-terminal of the amino acid sequences represented by SEQ ID NO:2-4.

As stated above, an amino acid sequence of a phosphorylated consensus sequence of CK1 (pS/T-X-X-S/T, pS/T-X-X-X-S) to which CK1 binds and which undergoes phosphorylation among the amino acid sequence of TDP-43 may also be used as a partial peptide of the present invention.

In addition, the protein and the partial peptide described above may, for example, be natural TDP-43 or a partial peptide thereof purified from a tissue or a cell such as the brain or spinal cord of a mouse or human, or TDP-43 produced by genetic engineering or a partial peptide thereof. Moreover, they may be synthesized by identifying their amino acid sequences, according to a known protein synthetic method such as a solid-phase method or by using a commercially available protein synthesizer.

In this regard, the phosphorylated amino acid residue may be Ser, Thr or Tyr residue, and preferably Ser or Thr residue. In a mutated amino acid sequence that has been mutated by substitution, if the substituting amino acid residue is Ser, Thr or Tyr, this amino acid residue may also be a target of phosphorylation.

More specifically, examples of phosphorylated partial peptides include the following peptides represented by SEQ ID NOS:5-11.

```
CASNAGS(PO3H2)GSGF              (SEQ ID NO: 5)

CNGGFGS(PO3H2)SMDSK             (SEQ ID NO: 6)

CNGGFGSS(PO3H2)MDSK             (SEQ ID NO: 7)

CNGGFGS(PO3H2)S(PO3H2)MDSK      (SEQ ID NO: 8)
```

-continued
```
CMDSKS(PO3H2)SGWGM              (SEQ ID NO: 9)

CMDSKSS(PO3H2)GWGM              (SEQ ID NO: 10)

CMDSKS(PO3H2)S(PO3H2)GWGM       (SEQ ID NO: 11)
```

In the above amino acid sequences, "(PO$_3$H$_2$)" indicates that the preceding amino acid residue has been phosphorylated. For example, in the above amino acid sequences, "S(PO$_3$H$_2$)" means that Ser has been phosphorylated.

The amino acid sequence represented by SEQ ID NO:5 has the 6th Ser residue phosphorylated and Cys linked to the N-terminal of the amino acid sequence represented by SEQ ID NO:2.

The amino acid sequence represented by SEQ ID NO:6 has the 6th Ser residue phosphorylated and Cys linked to the N-terminal of the amino acid sequence represented by SEQ ID NO:3.

The amino acid sequence represented by SEQ ID NO:7 has the 7th Ser residue phosphorylated and Cys linked to the N-terminal of the amino acid sequence represented by SEQ ID NO:3.

The amino acid sequence represented by SEQ ID NO:8 has the 6th and 7th Ser residues phosphorylated and Cys linked to the N-terminal of the amino acid sequence represented by SEQ ID NO:3.

The amino acid sequence represented by SEQ ID NO:9 has the 5th Ser residue phosphorylated and Cys linked to the N-terminal of the amino acid sequence represented by SEQ ID NO:4.

The amino acid sequence represented by SEQ ID NO:10 has the 6th Ser residue phosphorylated and Cys linked to the N-terminal of the amino acid sequence represented by SEQ ID NO:4.

The amino acid sequence represented by SEQ ID NO:11 has the 5th and 6th Ser residues phosphorylated and Cys linked to the N-terminal of the amino acid sequence represented by SEQ ID NO:4.

These phosphorylated TDP-43 or a partial peptide thereof may be phosphorylated natural TDP-43 purified from a tissue or a cell of the brain or spinal cord from mouse, human or the like having a TDP-43 proteinopathy lesion, or phosphorylated TDP-43 produced by genetic engineering. For example, a tissue of the brain or spinal cord with a TDP-43 proteinopathy lesion is fractionated into a soluble fraction and an insoluble fraction by using a surfactant such as Triton-X, Sarkosyl or the like. The insoluble fraction is further dissolved in urea, guanidine hydrochloride or the like, and allowed to bind to a column such as a heparin column or a binding resin to obtain phosphorylated TDP-43. Alternatively, phosphorylated TDP-43 used as an antigen may be synthesized by identifying its amino acid sequence and using a known protein synthetic method such as a solid-phase method or a commercially available protein synthetic device. The synthesized peptide may be linked with a carrier protein such as Keyhole Limpet Hemocyanin (KLH) or thyroglobulin to be used as an immunogen.

(2) Preparation of Polyclonal Antibody

The phosphorylated TDP-43 or the partial peptide thereof prepared as described above is administered alone or together with a carrier or a diluent to a warm-blooded animal such as rabbit, dog, guinea pig, mouse, rat or goat for immunization. A dosage of the antigen per animal is 1-10 mg without an adjuvant and 5-500 µg with an adjuvant. Examples of adjuvants include Freund's complete adjuvant (FCA), Freund's incomplete adjuvant (FIA) and aluminum hydroxide adjuvant. Immunization is performed mainly by intravenous, subcutaneous or intraperitoneal injection or the like. The intervals of immunizations are not particularly limited, and immunizations are performed at intervals of a few days to several weeks, preferably at intervals of 1 to 2 weeks, for 2-10 times, preferably for 3-5 times. The intervals of immunizations may be determined by those skilled in the art by considering the resulting antibody titer. Preferably, blood is sampled at the end of 3-4 times of subcutaneous immunizations to measure an antibody titer. The antibody titer in serum may be measured by ELISA (enzyme-linked immunosorbent assay), EIA (enzyme immunoassay), radioimmuno assay (RIA) or the like. After confirming that the antibody titer has increased to a sufficient level, whole blood can be collected to separate and purify the antibody according to a general method. For example, a serum containing the antibody of interest is passed through a column bound with unphosphorylated TDP-43 or unphosphorylated synthetic peptide (hereinafter, referred to as "unphosphorylated TDP-43"), and the passed-through fraction is collected, thereby obtaining a polyclonal antibody having enhanced specificity to phosphorylated TDP-43.

(3) Preparation of Monoclonal Antibody (i) Collection of Antibody-Producing Cell The phosphorylated TDP-43 or a partial peptide prepared as described above is administered alone or together with a carrier and a diluent to warm-blooded animals for immunization. A dosage of the antigen per animal is 1-10 mg without an adjuvant and 5-500 μg with an adjuvant. The type of adjuvant, an immunization method and immunization intervals employed are the same as those for the case of preparing a polyclonal antibody. One to thirty days, preferably 2-5 days after the final day of immunization, individuals with approved antibody titer are selected to collect antibody-producing cells. Examples of antibody-producing cells include spleen cells, lymph node cells and peripheral blood cells, but preferably spleen cells or lymph node cells.

(ii) Cell Fusion

In order to obtain a hybridoma, an antibody-producing cell and a myeloma cell are fused. The fusion process may be carried out by a known method, for example, by the method of Kohler et al. As the myeloma cell to be fused to the antibody-producing cell, a generally available cell line from an animal such as a mouse may be used. Preferably, the cell line used has drug selectivity, and cannot survive in a HAT selection medium (containing hypoxanthine, aminopterin and thymidine) in an unfused state but survives only when it is fused to the antibody-producing cell. Examples of myeloma cells include mouse myeloma cell lines such as PA1, P3U1, NSI/1-Ag4-1 and NSO/1, and rat myeloma cell lines such as YB2/0.

The cell fusion between the above-described myeloma cell and an antibody-producing cell is performed by mixing $1 \times 10^8$ to $5 \times 10^8$ antibody-producing cells with $2 \times 10^7$ to $10 \times 10^7$ myeloma cells (cell ratio of antibody-producing cells to myeloma cells being 1:1 to 1:10) in an animal cell culture medium such as a serum-free DMEM or an RPMI-1640 medium for fusion reaction in the presence of a cell fusion promoter. As a cell fusion promoter, an average molecular weight of 1000-6000 daltons of polyethylene glycol, Sendai virus or the like may be used. Alternatively, a commercially available cell fusion device employing electrostimulation (e.g., electroporation) may be used to fuse an antibody-producing cell with myeloma cells.

(iii) Selection and Cloning of Hybridoma

A hybridoma of interest is selected from the cells after the cell fusion treatment. According to such a method: a cell suspension is appropriately diluted, for example, in a 10-20% fetal bovine serum-containing RPMI-1640 medium; the resultant is seeded onto a microtiter plate at approximately $5 \times 10^7$ cells/well; a selection medium such as a HAT medium is added to each well; and thereafter the selection medium is appropriately exchanged for cultivation. As a result, cells that have grown after about 10 days following the beginning of culture with the selection medium may be obtained as hybridomas.

Then, the grown hybridomas are further subjected to screening. The hybridomas may be screened according to a general method without particular limitation. For example, a part of the culture supernatant contained in the hybridoma-culturing wells can be collected and screened by enzyme-linked immunosorbent assay, radioimmuno assay or the like. Specifically, an antigen is adsorbed onto a 96-well plate, which is then blocked with a calf serum. The culture supernatant of the hybridoma cells is allowed to react with a solid-phased antigen at 37° C. for an hour, followed by reaction with peroxidase-labeled anti-mouse IgG at 37° C. for an hour. Then, ortho-phenylenediamine is used as a substrate for color development. After terminating the reaction with an acid, absorbance at a wavelength of 490 nm can be measured for screening. Hybridomas that produce monoclonal antibodies that are positive in the above measurement are cloned by limiting dilution or the like. Eventually, a cell that produces a monoclonal antibody that specifically binds to phosphorylated TDP-43, i.e., a hybridoma, is established.

(iv) Collection of Monoclonal Antibody

As a method for collecting a monoclonal antibody from the established hybridoma, general cell cultivation, ascites production or the like may be employed. In the case of cell cultivation, the hybridoma is cultured in an animal cell culture medium such as a 10% fetal bovine serum-containing RPMI-1640 medium, an MEM medium or a serum-free medium, under general culture conditions (for example, at 37° C., 5% $CO_2$ concentration) for 7-14 days, thereby harvesting an antibody from the resulting culture supernatant. In the case of ascites production, about $2 \times 10^7$ hybridomas are administered intraperitoneally to an animal, for example, mice (BALB/c), syngeneic to the mammal from which myeloma cells are derived to proliferate the hybridomas in large amounts. After 1-2 weeks, ascites is collected. When purification of the antibody is required in the above antibody collection method, purification may be performed by appropriately selecting a known method such as ammonium sulfate precipitation, ion-exchange chromatography, gel filtration or affinity chromatography, or by combining these methods.

In this regard, a human type antibody may be acquired by using the immunogen (antigen) for immunizing a human antibody-producing transgenic non-human mammal according to an existing general antibody production method. A method for producing a human-type-antibody-producing non-human mammal, in particular a human-type-antibody-producing transgenic mouse, is known (Nature Genetics 7: 13-21 (1994); Nature Genetics 15: 146-156 (1997), etc.).

(4) Deposit of microorganism

A hybridoma that produces monoclonal antibody of the present invention (identified as: TDP43-pS409/410) was deposited with the International Patent organism Depositary Center of the National Institute of Advanced industrial Science and Technology (Central 6, 1-1-1, Higashi, Tsukuba, Ibaraki) on Jul. 3, 2008 as FERM ABP-10984 under the Budapest Treaty.

(5) Preparation of Recombinant Antibody

One of the preferable embodiments of an anti-phosphorylated-TDP-43 antibody of the present invention is a recombinant antibody. Examples of such recombinant antibodies include, without limitation, a chimeric antibody, a human type antibody and a humanized antibody.

A chimeric antibody (i.e., a humanized chimeric antibody) is an antibody in which a variable region of a mouse-derived antibody is linked (conjugated) to a human-derived constant region (see Proc. Natl. Acad. Sci. U.S.A. 81, 6851-6855, (1984), etc.). A chimera may readily be constructed by genetic recombination technique for obtaining such a linked antibody.

In order to produce a human type antibody, so-called CDR grafting (CDR implantation) technique may be employed. CDR grafting is a method for producing a rearranged variable region including a human-derived framework region (FR) and a mouse-derived CDR, by implanting a complementarity determining region (CDR) of a variable region from a mouse antibody into a human variable region. Subsequently, the human type rearranged human variable region is linked to a human constant region. A method for preparing such a human type antibody is well known in the art (see Nature, 321, 522-525 (1986); J. Mol. Biol., 196, 901-917 (1987); Queen C et al., Proc. Natl. Acad. Sci. USA, 86: 10029-10033 (1989); Japanese Patent Publication No. 2828340).

A humanized antibody (complete human antibody) is an antibody in which a hypervariable region, i.e., an antigen-binding site of V region, other parts of V region, and the constant region generally have the same structures as a human antibody. In this regard, the hypervariable site may be derived from other animals. Techniques for preparing a humanized antibody are known. In addition, a method for preparing a gene sequence common with human by a genetic engineering procedure has been established. A humanized antibody may be obtained, for example, by a method that employs a human antibody-producing mouse having a human chromosome fragment containing a gene of H-chain and L-chain of human antibody (see Tomizuka, K. et al., Nature Genetics, (1977) 16, 133-143; Kuroiwa, Y. et. al., Nuc. Acids Res., (1998) 26, 3447-3448; Yoshida, H. et. al., Animal Cell Technology: Basic and Applied Aspects, (1999) 10, 69-73 (Kitagawa, Y, Matuda, T. and Iijima, S. eds.), Kluwer Academic Publishers; Tomizuka, K. et. al., Proc. Natl. Acad. Sci. USA, (2000) 97, 722-727, etc.), or a method for obtaining a human antibody from a phage display selected from a human antibody library (see Wormstone, I. M. et. al, Investigative Ophthalmology & Visual Science., (2002) 43 (7), 2301-8; Carmen, S. et. al., Briefings in Functional Genomics and Proteomics, (2002) 1 (2), 189-203; Siriwardena, D. et. al., Opthalmology, (2002) 109 (3), 427-431, etc.).

Furthermore, according to the present invention, a chimeric antibody, a human type antibody or a humanized antibody may be prepared by using a hybridoma of the present invention (for example, hybridoma assigned Accession No. FERMABP-10984) or DNA, RNA or the like extracted from said hybridoma as a raw material, according to the above-described well-known method.

(6) Preparation of Antibody Fragment

Examples of the antibody fragments of the present invention include Fab (antigen-binding fragment), F(ab')$_2$, Fab', Fv, a diabody (dibodies), dsFv, a linear antibody, scFv (single chain Fv) or peptides including at least a complementarity determining region (CDR) as a part thereof.

Fab is an antibody fragment in which, among a fragment obtained by treating an antibody molecule with protease papain, about half of the N-terminal end of H-chain and the entire L-chain are linked via disulfide bond. Fab may be generated by inserting DNA encoding Fab of the antibody into an expression vector, and introducing the vector into a host organism for expression.

F(ab')$_2$ is an antibody fragment which, among a fragment obtained by treating an antibody molecule with protease pepsin, is slightly larger than one linked with Fab via a disulfide bond at the hinge region. F(ab')$_2$ may be generated by linking Fab via thioether bond or disulfide bond.

Fab' is an antibody fragment obtained by cleaving the disulfide bond at the above-mentioned hinge region of F(ab')$_2$. Fab' may be generated by inserting DNA encoding Fab' fragment of the antibody into an expression vector, and introducing the vector into a host organism for expression.

scFv is a polypeptide in which a single H-chain V region (VH) and a single L-chain V region (VL) are linked using an appropriate peptide linker, and an antibody fragment having an antigen-binding activity. seFv may be generated by acquiring cDNA encoding VH and VL of the antibody, constructing DNA coding for scFv, introducing the DNA into an expression vector, and introducing the expression vector into a host organism for expression.

A diabody is an antibody fragment with dimerized scFv having a divalent antigen-binding activity. The divalent antigen-binding activity may be identical or different from one another. A diabody may be generated by acquiring cDNA encoding for VH and VL of the antibody, constructing DNA encoding scFv such that the length of the amino acid sequence of the peptide linker is 8 residues or less, inserting the DNA into an expression vector, and introducing the expression vector into a host organism for expression.

dsFv has polypeptides having an amino acid residue of each of VH and VL substituted with a cysteine residue, which are bound via a disulfide bond between the cysteine residues. The amino acid residues substituted with cysteine residues may be selected based on the conformational prediction of the antibody (Protein Engineering, 7, 697-704, 1994). dsFv may be generated by acquiring cDNA coding for VH and VL of the antibody, constructing DNA encoding dsFv, inserting the DNA into an expression vector, and introducing the expression vector into a host organism for expression.

A peptide containing CDR is constructed to include at least one region of CDRs (CDRs 1-3) of V1-1 or VL. A peptide containing several CDRs may be bound directly or via an appropriate peptide linker. A peptide containing CDR may be generated by constructing DNA coding for CDR of VH and VL of the antibody, inserting the DNA into an expression vector, and introducing the expression vector into a host organism for expression. A peptide containing CDR may be generated by a chemical synthetic method such as an Fmoc method (fluorenylmethyloxycarbonyl method) or a tBoc method (t-butyloxy carbonyl method).

According to the present invention, an antibody fragment may be generated by using a hybridoma of the present invention (for example, hybridoma assigned Accession No. FERM ABP-10984) or DNA or RNA extracted from said hybridoma as a raw material according to the above-described well-known method.

4. Detection Agent and Method, and Diagnosis Agent and Method

An antibody of the present invention may be used as a reagent for detecting a TDP-43 proteinopathy lesion. A TDP-43 proteinopathy lesion can be observed in the brain, spinal cord and the like of a patient with a TDP-43 proteinopathy, and it presents emergence of abnormal TDP-43 protein aggregates such as ubiquitin-positive inclusions (NCIs). The lesion further presents TDP-43 accumulation, insolubilization, leakage or accompanying morphological or biochemical alteration of the cells or tissues.

Moreover, since an anti-phosphorylated TDP-43 antibody of the present invention is capable of detecting or quantifying phosphorylated TDP-43, it may be used as an agent for diagnosing a TDP-43 proteinopathy.

For detection of a TDP-43 proteinopathy lesion, an antibody that binds to a protein or a peptide having phosphorylated Ser409 and/or Ser410 is preferably used in terms of detection sensitivity.

A method for detecting a TDP-43 proteinopathy lesion or diagnosing a TDP-43 proteinopathy using an anti-phosphorylated-TDP-43 antibody may comprise, for example, the steps of:

(a) allowing reaction between an antibody of the present invention or a fragment thereof and a sample; and (b) allowing reaction between the antigen-antibody complex formed in step (a) and an antibody labeled for detection. At the end of the reaction, signals from the labeled antibodies are detected.

A method for detecting or diagnosing using a detection or diagnosis agent of the present invention may be any method as long as it is an antibody-employing assay, i.e., an immunological assay, examples being enzyme-linked immunosorbent assay (ELISA), fluorescent immunoassay, radioimmuno assay (RIA), luminescent immunoassay, an enzyme antibody method, a fluorescent antibody method, an immune nephelometry method, latex agglutination reaction, a latex turbidimetry method, hemaggiutination reaction, particle agglutination and western blot assay.

A sample subjected to a method of detection and/or quantification or diagnosis according to the present invention is not particularly limited as long as it is a biological sample that may possibly contain phosphorylated TDP-43, for example, nerve tissues (e.g., a tissue section of brain) and nerve cells of the brain, spinal cord or the like, and body fluid samples such as brain spinal cord fluid and blood.

When a method of detection and/or quantification or diagnosis according to the present invention is carried out by an immunoassay using a labeled antibody such as enzyme-linked immunosorbent assay, fluorescent immunoassay, radioimmuno assay or luminescent immunoassay, it may be performed by a sandwich method or a competitive method. In the case of a sandwich method, at least a solid-phased antibody or a labeled antibody is an antibody of the present invention.

A labeled antibody refers to an antibody that is labeled with a labeling substance, such labeled antibodies may be used for detecting or quantifying an antigen contained in a sample (for example, a nerve tissue or nerve cell of the brain or spinal cord, a body fluid sample such as brain spinal cord fluid or blood, a culture supernatant or a centrifuged supernatant).

A labeling substance that may be used with the present invention is not particularly limited as long as its presence can be detected through physical or chemical binding to the antibody. Specific examples of such labeling substances include enzymes, fluorescent substances, chemiluminescent substances, biotin, avidin and radioisotopes, more specifically, enzymes such as peroxidase, alkaline phosphatase, β-D-galactosidase, glucose oxidase, glucose-6-phosphate dehydrogenase, alcohol dehydrogenase, malate dchydrogenase, catalase, luciferase and acetylcholinesterase, fluorescent substances such as fluorescein isothiocyanate, dansyl chloride and tetramethyl rhodamine isothiocyanate, radioisotopes such as 3H, $^{14}$C, $^{125}$I and $^{131}$I, biotin, avidin and chemiluminescent substances. A binding method between a labeling substance and an antibody may be a known method such as glutaraldehyde method, maleimide method, pyridyl disulfide method or periodic acid method.

In this regard, although radioisotopes and fluorescent substances are capable of generating detectable signals by themselves, enzymes, chemiluminescent substances, biotin and avidin are unable to generate detectable signals by themselves and thus detectable signals are generated through further reaction with one or more other types of substances. For example, an enzyme requires at least one substrate, and various substances are used depending on the methods for measuring the enzymatic activity (colorimetric method, fluorescence method, bioluminescence method or chemiluminescence method, etc.). In the case of biotin, at least avidin or enzyme-modifying avidin is generally reacted therewith. If necessary, various chromogenic substances may further be used depending on the substrate.

A solid-phased antibody may be used for detecting, quantifying, separating or purifying an antigen in a sample (for example, a nerve tissue or a nerve cell of brain or spinal cord, a body fluid sample such as brain spinal cord fluid or blood, a culture supernatant and a centrifuged supernatant).

Examples of insoluble carriers that can be used for immobilizing the antibody include (i) a polystyrene resin, a polycarbonate resin, a silicon resin and a nylon resin, (ii) glass, (iii) a cellulose carrier, an agarose carrier, a polyacrylamide carrier, a dextran carrier, a polystyrene carrier, a polyvinyl alcohol carrier, a polyamino acid carrier and a porous silica carrier. These carriers may be used in a form of beads, a filter, a membrane or the like, or as a carrier for affinity chromatography.

5. Kit for Detection or Diagnosis

A kit for detecting a TDP-43 proteinopathy lesion or a kit for diagnosing a TDP-43 proteinopathy according to the present invention comprises an antibody of the present invention. An antibody used in this respect may be an immobilized antibody or a labeled antibody described above. For example, when an antibody of the present invention is used as a primary antibody, the kit of the present invention may comprise a secondary antibody for detecting a complex formed via antigen-antibody binding reaction. The kit of the present invention may comprise, other than these antibodies, various adjuvants in order to allow effective and simple use of the kit. Examples of such adjuvants include adjuvants generally used in a kit of immunoassay reagents such as a solubilizer for solubilizing a solid secondary antibody, a detergent used for washing an insolubilized carrier, a substrate for measuring an enzymatic activity when an enzyme is used as a labeling substance of the antibody, and a reaction terminator thereof.

6. Pharmaceutical Composition

A pharmaceutical composition of the present invention comprises an antibody of the present invention as an active element, and it is effective for preventing and treating relative nerve degeneration diseases such as TDP-43 proteinopathies, Alzheimer's disease, Lewy body dementia, and motor neuron disease. Examples of antibodies used include a human chimeric antibody or a humanized antibody. An additional example of an antibody used includes, a peptidized antibody or a bound body of a peptide thereof and a BBB permeable carrier, in order to allow passage through the blood-brain barrier (BBB).

An antibody of the present invention may be administered alone or together with a pharmaceutically acceptable carrier, a diluent or the like, in a single or several doses.

Herein, "pharmaceutically acceptable carriers" include an excipient, a diluent, a bulking filler, a disintegrant, a stabilizer, a preservative, a buffer, an emulsifier, an aromatic agent, a colorant, a sweetening agent, a thickening agent, a flavoring substance, a solubilizing adjuvant or other additives. With use of one or more of such carriers, a pharmaceutical composition may be prepared in a form of a tablet, a pill, powder, granulated powder, an injectable drug, a liquid drug, a capsule, a lozenge, an elixir, a suspension agent, an emulsifier, syrup or the like. Such pharmaceutical compositions may be administered either orally or parentally.

In the case of oral administration, various excipients such as microcrystalline cellulose, sodium citrate, calcium carbonate, dipotassium phosphate, glycine or the like may be used with a disintegrant, a binder or the like. Examples of disintegrants include starch, alginic acids and certain double silicates, while examples of binders include polyvinylpyrrolidone, sucrose, gelatin and gum arabic. In addition, lubricants such as magnesium stearate, sodium lauryl sulfate and talc are quite beneficial in forming tablets. When an aqueous suspension or elixir is employed for oral administration, if necessary, an emulsifier and a suspending agent may simultaneously be used together with a diluent such as water, ethanol, propylene glycol, glycerin, or a combination thereof.

Other forms for parenteral administration comprise a conventionally-formulated injectable drug containing one or more active substances.

In the case of an injectable drug, it may be produced, for example, by dissolving or suspending the antibody in a pharmaceutically acceptable carrier such as physiological saline or commercially available distilled water for injection to a concentration of 0.1 µg to 10 mg antibody/ml carrier. The thus-produced injectable drug may be administered to a human patient in need of treatment, for 10 µg to 50 mg/kg weight, preferably 100 µg to 2 mg/kg weight per dose for one to several times a day. However, the dosage is not limited to the above range, and it may vary depending on the weight and condition of a patient and individual administration route. The dosage may also fluctuate depending on the difference in patients' sensitivity to the drug, prescription of the drug, administration period and administration intervals. Therefore, in some cases, a suitable dosage may be lower than the lower limited of the above range.

Although exemplary forms of administration include intravenous injection, subcutaneous injection and intradermal injection, it is preferably intravenous injection. In addition, an injectable drug may possibly be prepared as a nonaqueous diluent (for example, propylene glycol, polyethylene glycol, a vegetable oil such as olive oil, or an alcohol such as ethanol), a suspension agent or an emulsion. Sterilization of such an injectable drug may be performed by filter sterilization through a bacteria-retaining filter, addition of disinfectant or by irradiation. An injectable drug may be produced in a form that is prepared before use. Specifically, a sterile solid composition is obtained by freeze-dry method, which may be dissolved in sterile distilled water for injection or other solvent before use.

Hereinafter, although the present invention will be described in detail by means of examples, the present invention should not be limited by these examples.

Example 1

Preparation of Antibody (1) Preparation of Antigen

As an antigen peptide for obtaining an antibody of the present invention, the following peptides containing a sequence (CASNAGSGSGF, CNGGFGSSMDSK or CMDSKSSGWGM) having cysteine linked to the N-terminal of amino acids 388-397, 398-408 or 405-414 of human TDP-43 (SEQ ID NO:1), and having a phosphorylated serine residue were synthesized by a solid-phase method (Sigma Genosys or ThermoQuest) [S($PO_3H_2$) represents phosphorylated serine]. Furthermore, unphosphorylated peptides having amino acid sequences represented by SEQ ID NOS:2-4 were also synthesized for use in column preparation, as controls or the like.

1. CASNAGS($PO_3H_2$)GSGF (SEQ ID NO: 5)
2. CNGGFGS($PO_3H_2$)SMDSK (SEQ ID NO: 6)
3. CNGGFGSS($PO_3H_2$)MDSK (SEQ ID NO: 7)
4. CNGGFGS($PO_3H_2$)S($PO_3H_2$)MDSK (SEQ ID NO: 8)
5. CMDSKS($PO_3H_2$)SGWGM (SEQ ID NO: 9)
6. CMDSKSS($PO_3H_2$)GWGM (SEQ ID NO: 10)
7. CMDSKS($PO_3H_2$)S($PO_3H_2$)GWGM (SEQ ID NO: 11)

(2) Immunization

The above-described synthetic peptide was conjugated with thyroglobulin or KLH according to a conventional method to be used as an antigen. One ml of 1 mg/ml antigen peptide in a physiological saline solution containing the antigen peptide and 1 ml of Freund's complete adjuvant (Difco) were mixed, emulsified by ultrasonic treatment, and used for immunization to several places of the back of a rabbit (New Zealand white, weight 2.5 kg, female) Two weeks after the primary immunization, 0.5 ml of 1 mg/ml antigen peptide in saline solution and 1 ml of Freund's incomplete adjuvant were mixed, emulsified by ultrasonic treatment and used as a booster. A week after the immunization, blood was drawn, which was left to stand at room temperature for an hour, then at 4° C. overnight, and centrifuged at 5000×g for 10 minutes, thereby obtaining an antiserum.

(3) Purification of Antibody

In order to purify the antibody, a column was prepared in which about 2 ml of Formyl-Cellulofine (Seikagaku Co.) or Toyopearl AF-Tresyl-650M (Tosoh) was reacted with about 2 mg of an unphosphorylated synthetic peptide having an amino acid sequence of the amino acids 388-397, 398-408 or 405-414 of TDP-43. Two ml of the antiserum was circulated in this column for 10-20 hours, and antibodies that did not adsorbed onto the column were used as anti-phosphorylated TDP-43 antibodies.

Among the anti-phosphorylated TDP-43 antibodies, a polyclonal antibody for a peptide having phosphorylated Ser409 and Ser410 was named pSer409/410 polyclonal antibody.

Example 2

Preparation of Monoclonal Antibody (1) Preparation of Hybridoma

Primary and booster immunizations were performed according to the method in "Example 1, (2) Immunization" above.

Three days after the final immunization, spleen was collected from the immunized mice. The collected spleen cells and myeloma cell line were mixed at a ratio of 5:1 for cell fusion by polyethylene glycol method. A selection medium containing HAT (aminopterin, hypoxanthine, and thymidine) was used for cultivation in a 5% $CO_2$ incubator. Hybridomas proliferated during 7-14 days of cultivation were screened.

Screening was performed by applying Triton insoluble fraction from FTLD patient brain to a PLL-coated glass slide, with which the culture supernatant of the hybridoma was reacted, and clones producing an antibody that reacts with an abnormal structure (i.e., that stains an abnormal structure)

were selected. Thereafter, clones of hybridoma producing the monoclonal antibody of the present invention were obtained by limiting dilution.

(2) Preparation of Monoclonal Antibody

A monoclonal antibody of the present invention was obtained by intraperitoneally administering the clones of the hybridoma prepared by the above method to BALB/c mice and collecting ascites, or by preparing a highly-concentrated culture supernatant.

Specifically, $1 \times 10^7$ clones of the hybridoma prepared by the above method were intraperitoneally administered to BALB/c mice that had been administered with 2,6,10,14-tetramethylpentadecane (pristane) beforehand (10 days in advance), and ascites were collected after 2 weeks.

The thus-obtained monoclonal antibody was named pSer409/410 monoclonal antibody.

(3) Deposit of Hybridoma

Among the hybridomas obtained according to the above method, hybridomas that produce pSer409/410 monoclonal antibody were named "TDP43-pS409/410" and deposited with the International Patent organism Depository Center of the National Institute of Advanced industrial Science and Technology (Central 6, 1-1-1, Higashi, Tsukuba, Ibaraki) on Jul. 3, 2008 (Accession Number: FERM ABP-10984).

Example 3

Examination of Specificity of Antibody by Western Blotting Assay and ELISA Assay Whether or not each of the antibodies prepared in Example 1 specifically react with a phosphorylated antigen peptide was confirmed by western blotting assay and ELISA assay.

In an examination by western blotting assay, two types of phosphorylated recombinant human TDP-43 and unphosphorylated TDP-43 (control) were used as antigen peptides, while an antibody for a peptide with phosphorylated Ser409 (pSer409 (pS409)), an antibody for a peptide with phosphorylated Ser410 (pSer410 (pS410)) and an antibody for a peptide with phosphorylated Ser409 and Ser410 (pSer409,410) were used as antibodies. In addition, an antibody for an unphosphorylated TDP-43 peptide having an amino acid sequence of amino acids 405-414 was used as a control.

The above antigen peptides were separated by SDS-PAGE, transferred onto a PVDF membrane, and reactivity between the transferred peptide and the above antibodies were examined. As a result, these antibodies reacted with recombinant human TDP-43 that had been phosphorylated by CK1, but did not react with TDP-43 that was not phosphorylated by CK1 (FIG. 1). In FIG. 1, "CK1" refers to casein kinase 1 and "CK2" refers to casein kinase 2, and indicate phosphorylation by CK1 and CK2, respectively.

Figure 2:
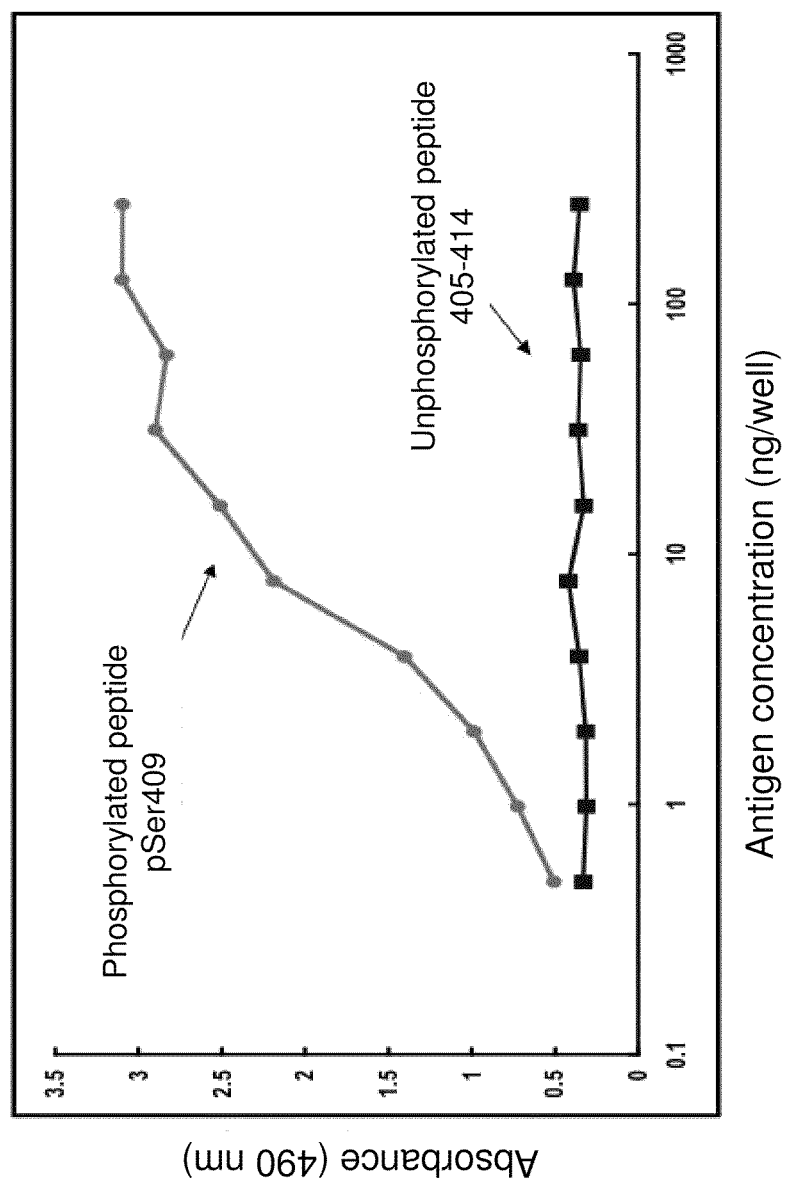
FIG. 2 is a diagram showing the results from examination of reactivity (specificity) of an anti-pSer409-phosphorylated-peptide antibody by ELISA assay.
Figure 3:
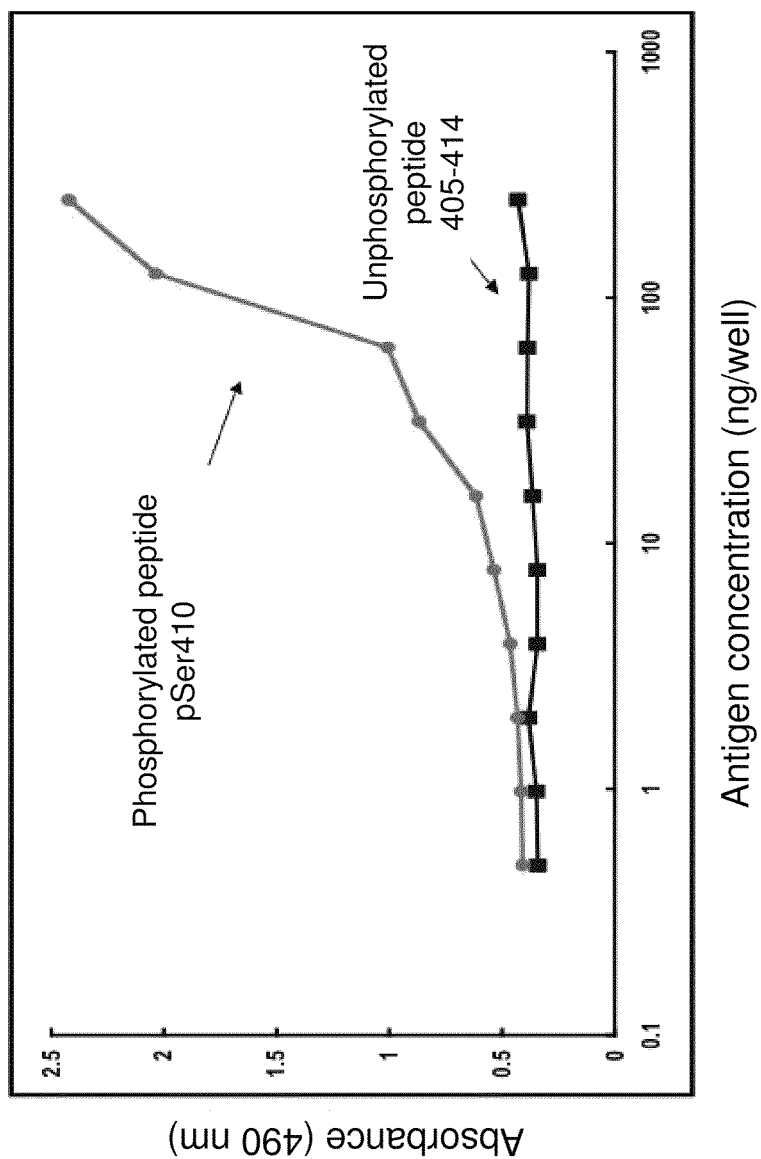
FIG. 3 is a diagram showing the results from examination of reactivity (specificity) of an anti-pSer410-phosphorylated-peptide antibody by ELISA assay.
Figure 4:
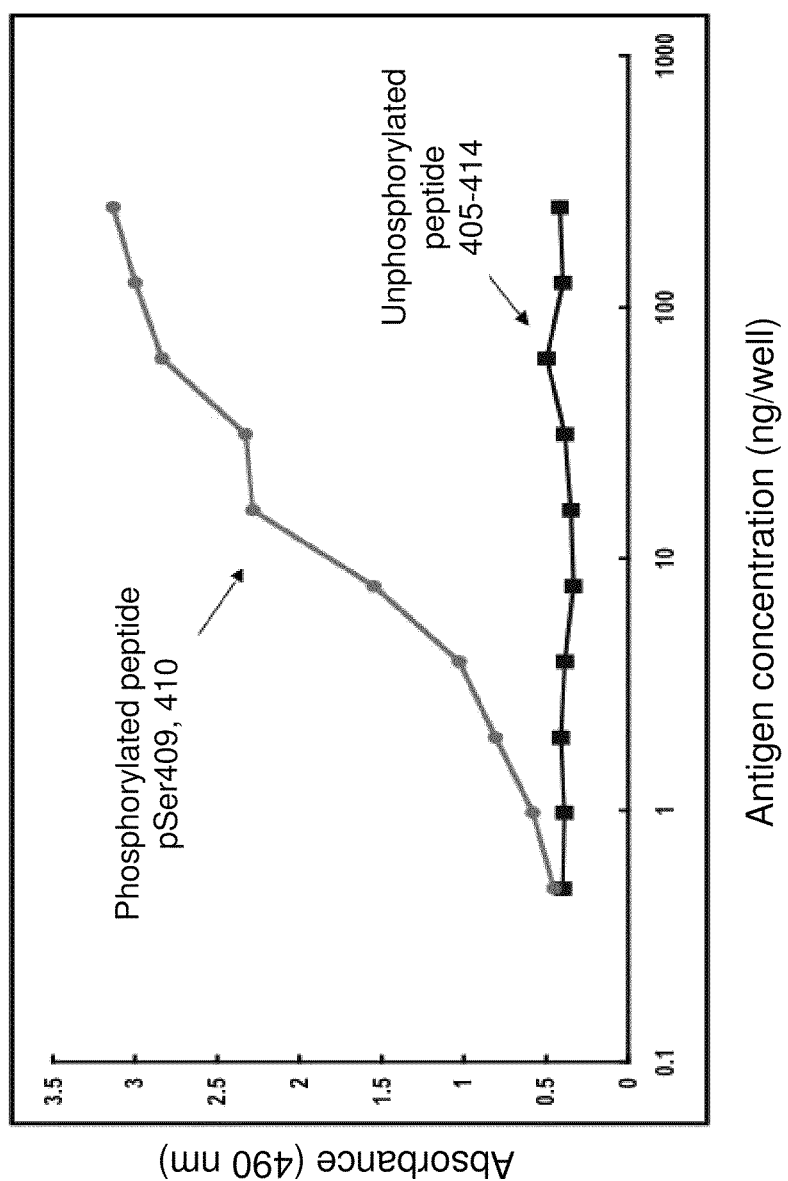
FIG. 4 is a diagram showing the results from examination of reactivity (specificity) of an anti-pSer409,410-phosphorylated-peptide antibody by ELISA assay.

In an examination by ELISA assay, 5 μg/well of an unphosphorylated peptide or an antigen peptide was adsorbed onto the bottom surfaces of a 96-well plate (Sumitomo Bakelite) according to a conventional method, which was then reacted with 500-1000-fold dilution of the antibody prepared in Example 1, and allowed to develop color by a conventional method. As a result, no reaction was observed with an unphosphorylated peptide but strong reactivity was observed with the antigen peptides (FIGS. 2-4).

Example 4

Immunohistostaining of Antibody

Figure 5:
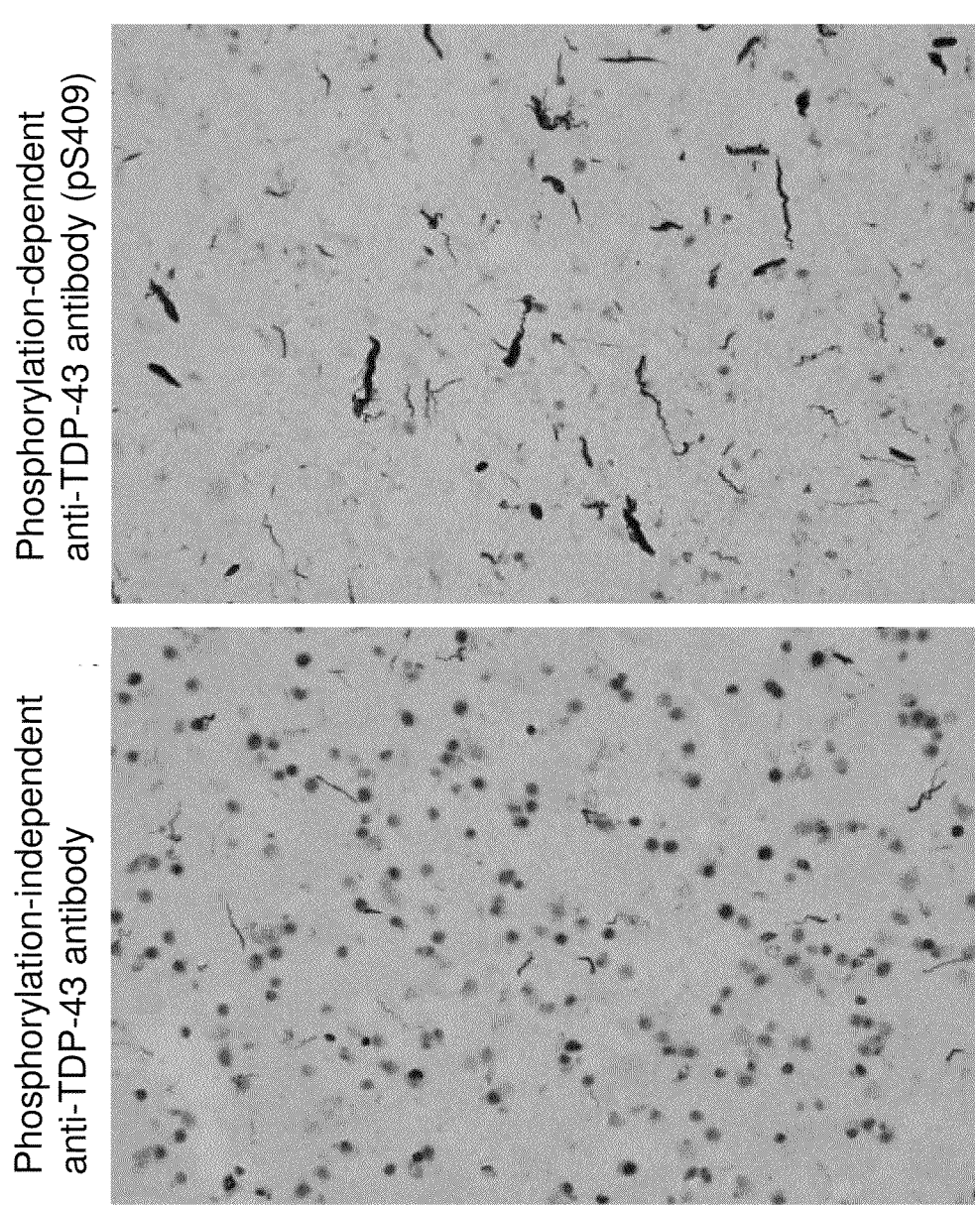
FIG. 5 is a view showing the results of immunostaining FTLD brain tissues using a commercially available TDP-43 antibody and pS409 antibody.

Cerebral cortices collected from FTLD patients were formalin-fixed, sliced into a thickness of 50 micrometers, which were immunostained by an avidin/biotin complex method using a commercially available anti-human-TDP43 antibody (ProteinTech) (FIG. 5, "phosphorylation-independent anti-TDP-43 antibody") and an anti-phosphorylated TDP-43 antibody of the present invention (FIG. 5, "phosphorylation-dependent anti-TDP-43 antibody (pS409)"), and allowed to develop color using diaminobenzidine.

As a result, when an anti-phosphorylated TDP-43 antibody of the present invention was used, strong positive reaction (brown) was observed in the cerebral cortices, with degenerating nerve spicule-like, spherical or dot TDP-43 proteinopathy lesions. Meanwhile, little reaction was observed with normal TDP-43 localized in the cellular nuclei (FIG. 5, right panel). On the other hand, when a commercially available anti-human TDP43 antibody was used, reaction with normal TDP-43 localized in the cellular nuclei was observed (FIG. 5, left panel). Moreover, skein-like inclusions that appear in amyotrophic lateral sclerosis (ALS) patients also exhibited strong positive reaction against the antibody of the present invention. The antibody of the present invention detected wider range of TDP-43 abnormity with higher sensitivity than the commercially available anti-TDP-43 antibody.

Example 5

Detection of Abnormal TDP-43 by ELISA Assay and Western Blotting Assay (1) Preparation of Sample Cerebral cortices (0.5 g) collected from patients with FTLD, ALS, FTLD having progranulin mutation (mPGRN), Alzheimer's disease (AD) and Lewy body dementia (DLB) with TDP-43 accumulation, and cerebral cortices (0.5 g) collected from patients without these diseases or healthy subjects (Control or Con) were each homogenized in 5 mL Buffer A (10 mM Tris-HCl, pH7.5, 1 mM EGTA, 0.8M NaCl, 10% sucrose), and centrifuged at 35000 rpm for 20 minutes. Thereafter, the precipitates were homogenized in 5 mL of the same Buffer A containing 1% Triton, centrifuged at 35000 rpm for 20 minutes. The resulting precipitate was further homogenized in 5 mL of the same Buffer A containing 1% Sarkosyl and centrifuged at 35000 rpm for 20 minutes. The resulting precipitate was dissolved in 1 mL of 8M urea solution or 1% SDS solution, and subjected to detection by ELISA or western blotting. Dephosphorylation was perfoinied with lambda protein phosphatase (λPPase) at 30° C. for two hours following dialysis of the 8M urea fraction.

(2) Detection by ELISA Assay

Insoluble fractions of normal brain free from TDP-43 accumulation (Control), and FTLD brain with TDP-43 accumulation (FTLD) were serial diluted from 4 μg in 50 mM Tris-HCl Buffer (pH 8.8) and used to coat a 96-well plate at 4° C. overnight. Thereafter, commercially available TDP-43 antibody, pSer409/410 polyclonal antibody (Example 1) and pSer409/410 monoclonal antibody (Examples 2) of the present invention were allowed to react for two hours as primary antibodies, and a peroxidase-labeled secondary antibody were further allowed to react for another two hours, followed by color development with ortho-phenylenediamine as a substrate for detection.

Figure 6:
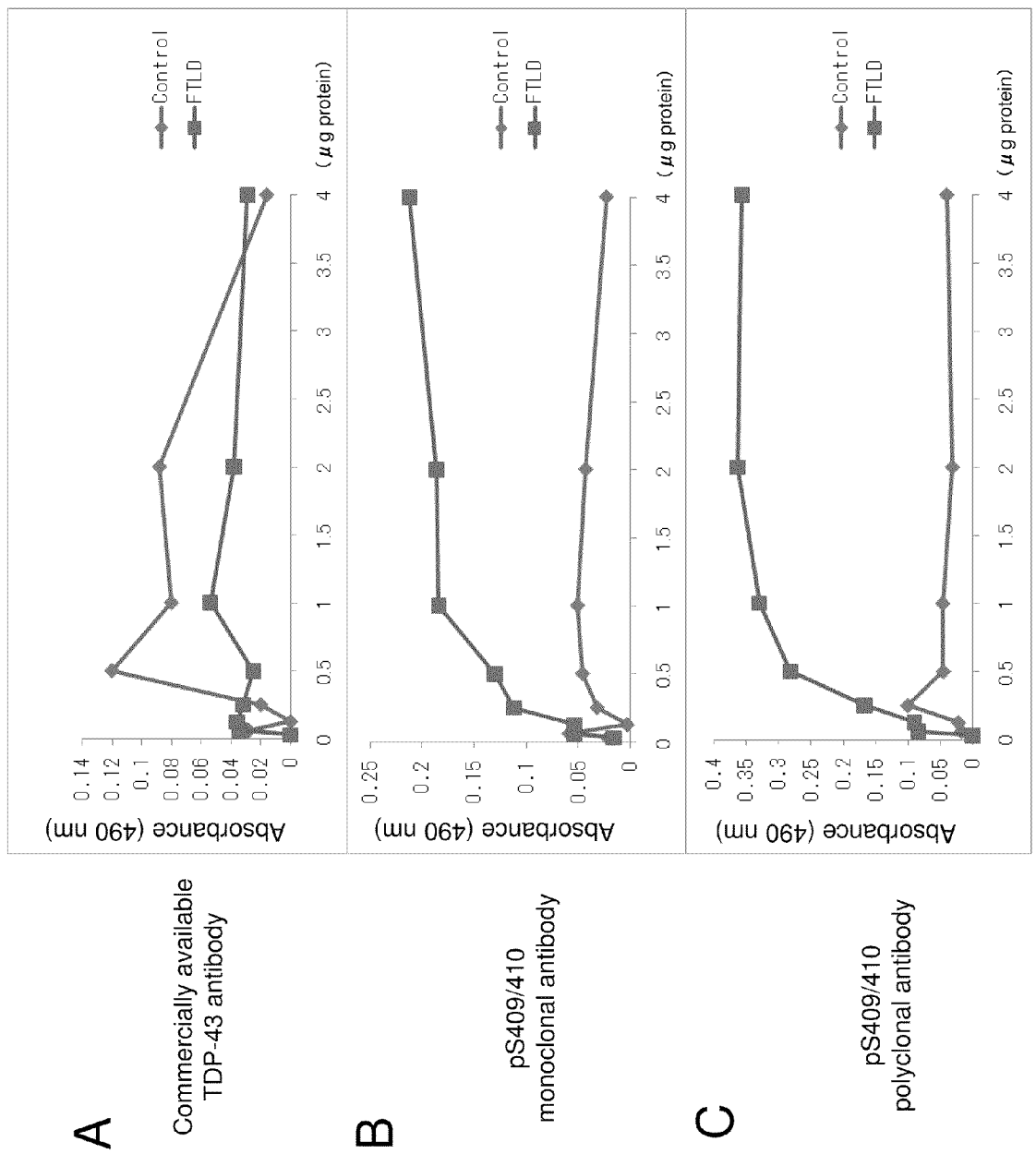
FIG. 6 is a view showing the results of detecting abnormal TDP-43 by ELISA assay.

With the commercially available antibody, no difference was detected between normal (Control) and FTLD (FIG. 6, Panel A). On the other hand, with the anti-phosphorylated-TDP-43 antibody of the present invention, strong positive reaction against the samples from FTLD patients were observed for both pSer409/410 monoclonal antibody (FIG. 6, Panel B) and pSer409/410 polyclonal antibody (FIG. 6, Panel C) where the reaction was dose-dependent.

(3) Detection by Western Blotting (1)

Insoluble fractions of normal brain free from TDP-43 accumulation (Control), FTLD brain with TDP-43 accumulation (FTLD) and brain from ALS patients were electrophoresed in 10% polyacrylamide gel. The separated protein was transferred onto a PVDF membrane and allowed to react with a commercially available antibody or pSer409/410 monoclonal antibody of the present invention. Western blotting was performed by employing an avidin/biotin complex method as described above, and color was developed with diaminobenzidine.

Figure 7:
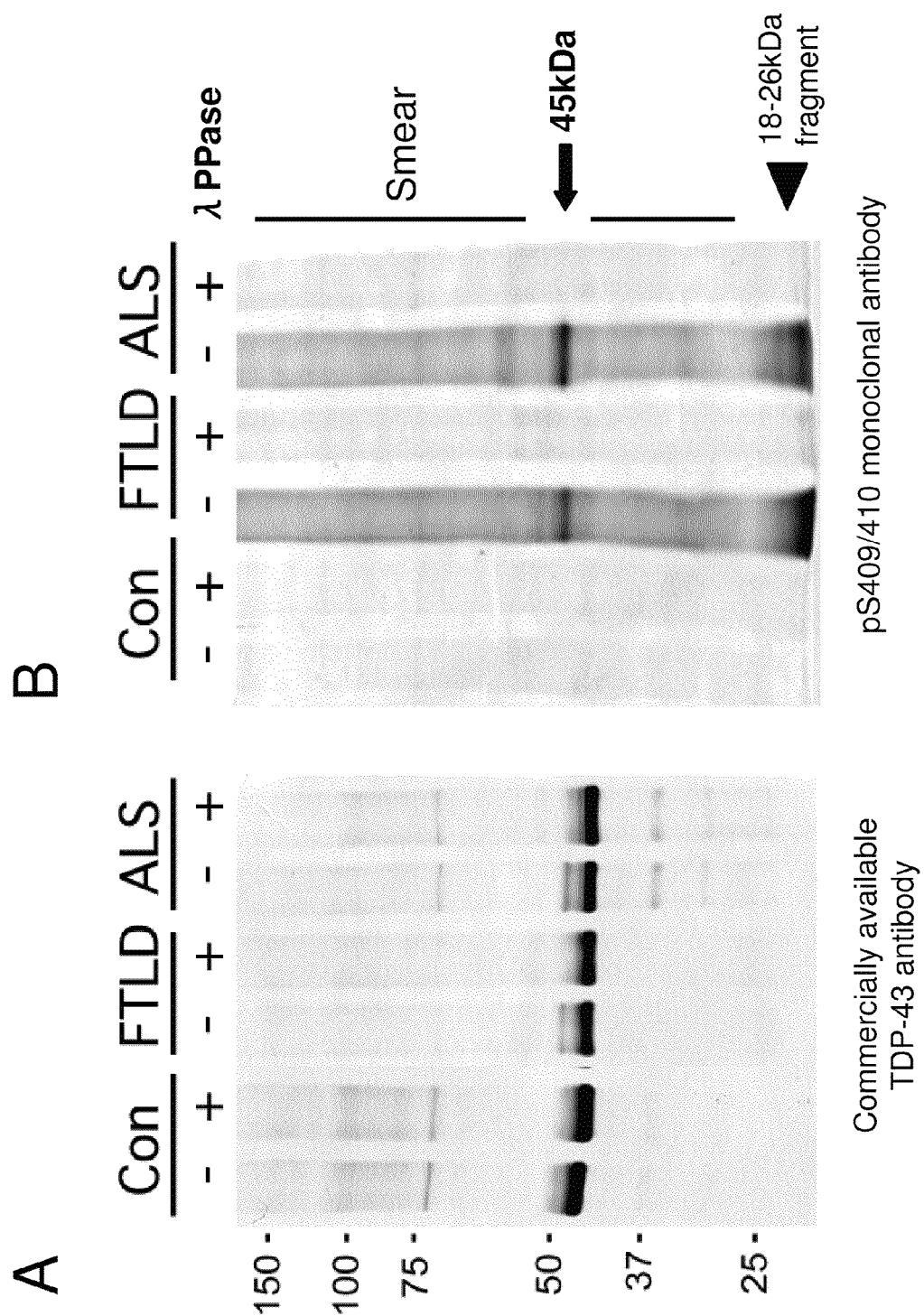
FIG. 7 is a view showing the results of detecting abnormal TDP-43 by western blotting assay.

As a result, with the commercially available antibody, the band of normal TDP-43 that migrated to 43 kDa was strongly recognized, and distinction between normal TDP-43 and abnormal TDP-43 was difficult (FIG. 7, Panel A). On the other hand, the pSer409/410 monoclonal antibody of the present invention did not react with the normal TDP-43 band, while it specifically detected abnormal TDP-43 bands such as 45 kDa band and 18-26 kDa band observed in FTLD or ALS patients, as well as reaction that stained the entire lane like a smear (in the figure, "smear") (FIG. 7, Panel B). Since this reaction was quenched by dephosphorylation treatment with lambda protein phosphatase (in the figure, "λPPase") (FIG. 7, Panel "+"), the antibody was confirmed to specifically recognize phosphorylated TDP-43 accumulated in patients' brains.

(4) Detection of TDP-43 Fragment by Western Blotting (2)

Lesions of TDP-43 accumulation are known to exhibit different pathologies depending on the disease, which fall into Type 1 with the majority of the lesions being intraspicular inclusions, Type 2 with many round intracellular inclusions, and Type 3 with both of them: Sporadic FTLD is classified as Type 1; FTLD-MND and ALS as Type 2; and familial FTLD with PGRN mutation (mPGRN) as Type 3 (FIG. 8, Panel A).

Figure 8:
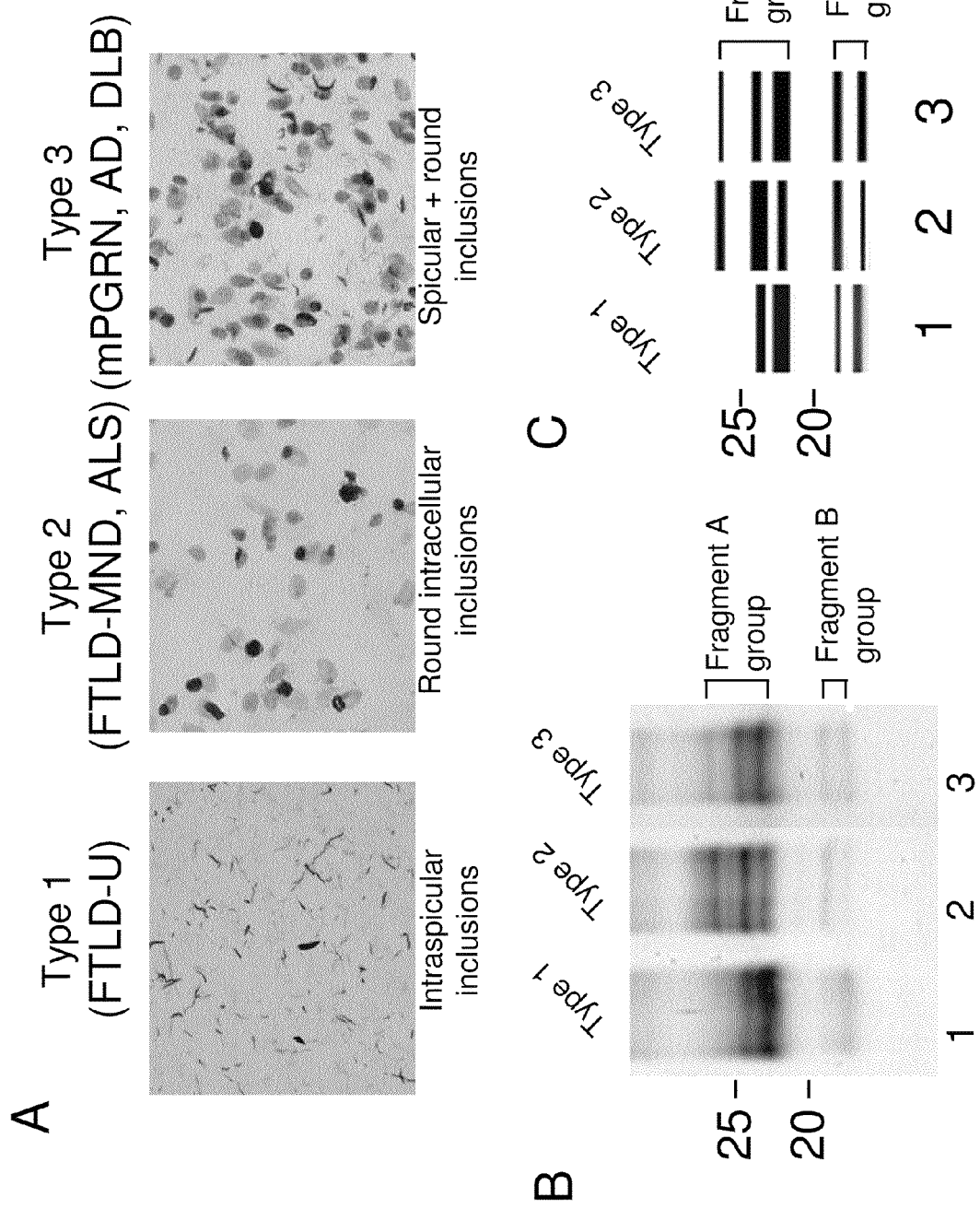
FIG. 8 is a view showing the results of detecting abnormal TDP-43 by western blotting assay.

In addition, the cases of Alzheimer's disease (AD) and Dementia with Lewy bodies (DLB) showing TDP-43 accumulation have been reported recently, which exhibited pathology of Type 3 (FIG. 8, Panel A). Insoluble fractions prepared from these patients' brains as described above were subjected to electrophoresis with 15% polyacrylamide gel. The separated protein was transferred onto a PVDF membrane, and allowed to react with the pSer409/410 antibody of the present invention to examine the difference.

As a result, for the sporadic FTLD cases (Type 1), two major bands at 23 and 24 kDa (fragment A group) and two weak bands at 18 and 19 kDa (fragment B group) were detected. Meanwhile, for FTLD-MND and ALS cases (Type 2), three major bands at 23, 24 and 26 kDa (fragment A group) and two weak bands at 18 and 19 kDa (fragment B group) were detected. The 23 kDa band was the strongest for the sporadic FTLD cases whereas the 24 kDa hand was the strongest for the FTLD-MND and ALS cases.

Furthermore, mPGRN cases and AD and DLB cases with TDP-43 accumulation (Type 3) stayed in the middle of sporadic FTLD and FTLD-MND/ALS cases (FIG. 8, Panels B and C).

The present example proves that the antibody of the present invention is capable of specifically recognizing phosphorylated TDP-43. In addition, use of the antibody of the present invention was found to allow specific detection of a TDP-43 proteinopathy lesion, and further to specify the type of a TDP-43 proteinopathy lesion.

Hence, the antibody of the present invention is useful as an agent for detecting phosphorylated TDP-43, an agent for detecting a TDP-43 proteinopathy lesion and an agent for diagnosing a TDP-43 proteinopathy.

INDUSTRIAL APPLICABILITY

The present invention is capable of providing an antibody that binds specifically to an abnormal TDP-43 protein aggregate such as ubiquitin-positive inclusions detected in an organism. The antibody of the present invention can specifically bind to phosphorylated TDP-43 or to a peptide having a part thereof that constitutes an abnormal TDP-43 protein aggregate found in a TDP-43 proteinopathy patient. Accordingly, the antibody of the present invention is useful for diagnosing or treating a TDP-43 proteinopathy such as FTLD or ALS.

Sequence Listing: Free Text
SEQ ID NO:2: Synthetic peptide
SEQ ID NO:3: Synthetic peptide
SEQ ID NO:4: Synthetic peptide
SEQ ID NO:5: Phosphorylated synthetic peptide
SEQ ID NO:6: Phosphorylated synthetic peptide
SEQ ID NO:7: Phosphorylated synthetic peptide
SEQ ID NO:8: Phosphorylated synthetic peptide
SEQ ID NO:9: Phosphorylated synthetic peptide
SEQ ID NO:10: Phosphorylated synthetic peptide
SEQ ID NO:11: Phosphorylated synthetic peptide
SEQ ID NO:12: Phosphorylated consensus sequence
SEQ ID NO:13: Phosphorylated consensus sequence

The invention claimed is:

1. A purified antibody that binds specifically to the following protein (a) or (b):
   (a) a protein consisting of an amino acid sequence in which at least one amino acid residue selected from the group consisting of amino acid residues 393, 403, 404, 409 and 410 of the amino acid sequence represented by SEQ ID NO:1 is phosphorylated; or
   (b) a phosphorylated partial peptide selected from the group consisting of amino acid sequences set forth in SEQ ID No: 5, SEQ ID NO: 6, SEQ ID NO: 7, SEQ ID NO: 8, SEQ ID NO: 9, SEQ ID NO: 10, and SEQ ID NO: 11,
   wherein said antibody does not bind with an unphosphorylated amino acid sequence represented by SEQ ID NO:1 and with an unphosphorylated partial peptide selected from the group consisting of amino acid sequences set for the in SEQ ID NO: 2, SEQ ID NO: 3, and SEQ ID NO: 4.

2. The purified antibody according to claim 1, which can bind to a site of the protein (a) or the partial peptide (b) that has been structurally altered by phosphorylation.

3. The purified antibody according to claim 1, wherein the phosphorylation is induced by casein kinase 1.

4. The purified antibody according to claim 1, wherein the antibody is a monoclonal antibody.

5. The purified antibody according to claim 1, wherein the antibody is a polyclonal antibody.

6. A hybridoma that produces the antibody according to claim 4.

7. An agent for detecting phosphorylated TDP-43, comprising the purified antibody according to claim 1.

8. An agent for detecting a TDP-43 proteinopathy lesion, comprising the purified antibody according to claim 1.

9. An agent for diagnosing a TDP-43 proteinopathy, comprising the purified antibody according to claim 1.

10. A pharmaceutical composition comprising:
    the purified antibody according to claim 1 as an active element; and
    a pharmaceutically acceptable carrier.

11. The antibody according to claim 1, wherein said at least one amino acid residue is at least one selected from the group consisting of amino acid residues 409 and 410 of the amino acid sequence represented by SEQ ID NO:1.

* * * * *